US010221384B2

(12) United States Patent
Akerstrom et al.

(10) Patent No.: US 10,221,384 B2
(45) Date of Patent: *Mar. 5, 2019

(54) BIOREACTOR SYSTEM WITH A TEMPERATURE SENSOR

(71) Applicant: GE Healthcare Bio-Sciences AB, Uppsala (SE)

(72) Inventors: Patrik Akerstrom, Uppsala (SE); Patric Fricking, Uppsala (SE); Lars Johan Carlsson, Kungsangen (SE); Hakan Wahlnas, Uppsala (SE)

(73) Assignee: GE HEALTHCARE BIO-SCIENCES AB, Uppsala (SE)

( * ) Notice: Subject to any disclaimer, the term of this patent is extended or adjusted under 35 U.S.C. 154(b) by 0 days.

This patent is subject to a terminal disclaimer.

(21) Appl. No.: 14/899,128

(22) PCT Filed: Jun. 16, 2014

(86) PCT No.: PCT/SE2014/050728
§ 371 (c)(1),
(2) Date: Dec. 17, 2015

(87) PCT Pub. No.: WO2014/204384
PCT Pub. Date: Dec. 24, 2014

(65) Prior Publication Data
US 2016/0145561 A1    May 26, 2016

(30) Foreign Application Priority Data
Jun. 17, 2013  (SE) ..................................... 1350732

(51) Int. Cl.
*C12M 1/00*  (2006.01)
*C12M 3/00*  (2006.01)
(Continued)

(52) U.S. Cl.
CPC ............ *C12M 41/12* (2013.01); *C12M 23/14* (2013.01); *C12M 23/48* (2013.01); *G01K 1/143* (2013.01); *G01K 1/16* (2013.01)

(58) Field of Classification Search
CPC ...... C12M 23/02; C12M 23/44; C12M 23/26; C12M 23/14; C12M 23/48; C12M 41/12; C12M 23/50; C12M 23/56; C12M 47/20; G01K 1/143; G01K 1/16; G01K 1/20; G01K 1/22; G01K 1/24
See application file for complete search history.

(56) References Cited

U.S. PATENT DOCUMENTS

| 4,407,141 A | 10/1983 | Paddock |
| 5,193,912 A | 3/1993 | Saunders |
(Continued)

FOREIGN PATENT DOCUMENTS

| CN | 2800245 Y | 7/2006 |
| CN | 201569039 U | 9/2010 |
(Continued)

OTHER PUBLICATIONS

International Search Report and Written Opinion issued in connection with corresponding PCT application PCT/SE2014/050728 dated Sep. 16, 2014.
(Continued)

*Primary Examiner* — Gautam Prakash
*Assistant Examiner* — Lydia Edwards
(74) *Attorney, Agent, or Firm* — Wood IP LLC

(57) ABSTRACT

A bioreactor system comprising a base station comprising a control system, a tray arranged to be provided on the base station and arranged to house a bioreactor bag, wherein said base station comprises at least one temperature sensor means and in that said tray comprises at least one opening for receiving said temperature sensor means such that it will contact a surface of a bioreactor provided in the tray.

12 Claims, 2 Drawing Sheets

(51) Int. Cl.
  *C12M 1/34* (2006.01)
  *G01K 1/14* (2006.01)
  *G01K 1/16* (2006.01)

(56) References Cited

U.S. PATENT DOCUMENTS

| | | | |
|---|---|---|---|
| 6,384,380 B1* | 5/2002 | Faries, Jr. | A61G 12/001 |
| | | | 219/385 |
| 2005/0272146 A1 | 12/2005 | Hodge et al. | |
| 2007/0215018 A1* | 9/2007 | Faries, Jr. | A61B 50/10 |
| | | | 109/23 |
| 2010/0327849 A1* | 12/2010 | Kamen | A61M 1/1605 |
| | | | 324/105 |
| 2012/0258441 A1 | 10/2012 | Gebauer | |
| 2015/0204733 A1* | 7/2015 | Newell | G01K 1/14 |
| | | | 374/141 |

FOREIGN PATENT DOCUMENTS

| | | |
|---|---|---|
| CN | 202041328 U | 11/2011 |
| CN | 102656282 A | 9/2012 |
| CN | 202543215 U | 11/2012 |
| EP | 3011007 A1 | 4/2016 |
| JP | 2001235444 A | 8/2001 |
| JP | 2007174982 A | 7/2007 |
| JP | 2008067622 A | 3/2008 |
| WO | 2008102249 A1 | 8/2008 |
| WO | 2011003615 A2 | 1/2011 |
| WO | 2014/204384 A1 | 12/2014 |

OTHER PUBLICATIONS

International Preliminary Report on Patentability Received for PCT Patent Application No. PCT/SE2014/050728, dated Dec. 30, 2015, 6 Pages.

Office Action Received for Chinese Patent Application No. 201480034248.8, dated Jul. 7, 2017, 14 pages (8 Pages of English translation + 6 Pages official copy).

Office Action received for Chinese Patent Application No. 201480034248.8, dated Dec. 2, 2016, 13 pages.

Extended European Search Report Received for European Patent Application No. 14813324.2, dated Feb. 17, 2017, 10 pages.

English translation of Chinese First Search Report from CN Appl. No. 201480034248.8, filed Jun. 16, 2014.

* cited by examiner

BIOREACTOR SYSTEM WITH A TEMPERATURE SENSOR

TECHNICAL FIELD OF INVENTION

Embodiments of the present invention relate to a temperature sensor means and a bioreactor system comprising such a temperature sensor means.

BACKGROUND OF THE INVENTION

Measuring temperatures in bioreactors can be done invasively or noninvasively. Noninvasive measurements are preferred in many cases because the content of the bioreactor should not be contaminated. Temperature sensors provided outside the bioreactor have been used. A problem with such temperature sensors is that ambient temperature will affect the measured temperature.

SUMMARY OF THE INVENTION

The object of embodiments of the present invention is to provide reliable temperature measurements and to provide bioreactor systems that are easy to handle.

This is achieved in a bioreactor system comprising a base station comprising a control system, a tray arranged to be provided on the base station and arranged to house a bioreactor bag, wherein the base station comprises at least one temperature sensor means and in that the tray comprises at least one opening for receiving the temperature sensor means such that it will contact a surface of a bioreactor provided in the tray. Hereby a flexible and easy to handle bioreactor system with reliable temperature measuring capabilities is achieved.

Furthermore the circulation in the bioreactor is not affected by the temperature sensor. Another advantage is that only the base station and not the tray holding the bioreactor need to be considered for calibration. Furthermore a bioreactor system providing reliable temperature measurements with very limited influence from ambient temperature is achieved.

Further embodiments are described in the dependent claims.

DETAILED DESCRIPTION

Figure 1:
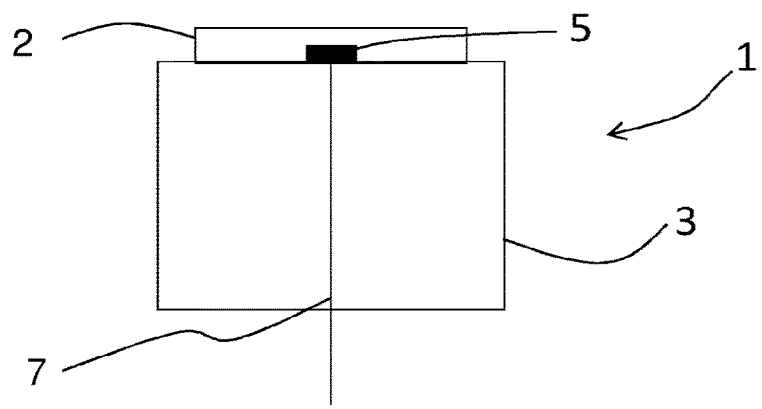
FIG. 1 shows schematically a temperature sensor means according to one embodiment of the invention.
Figures 2A, 2B:
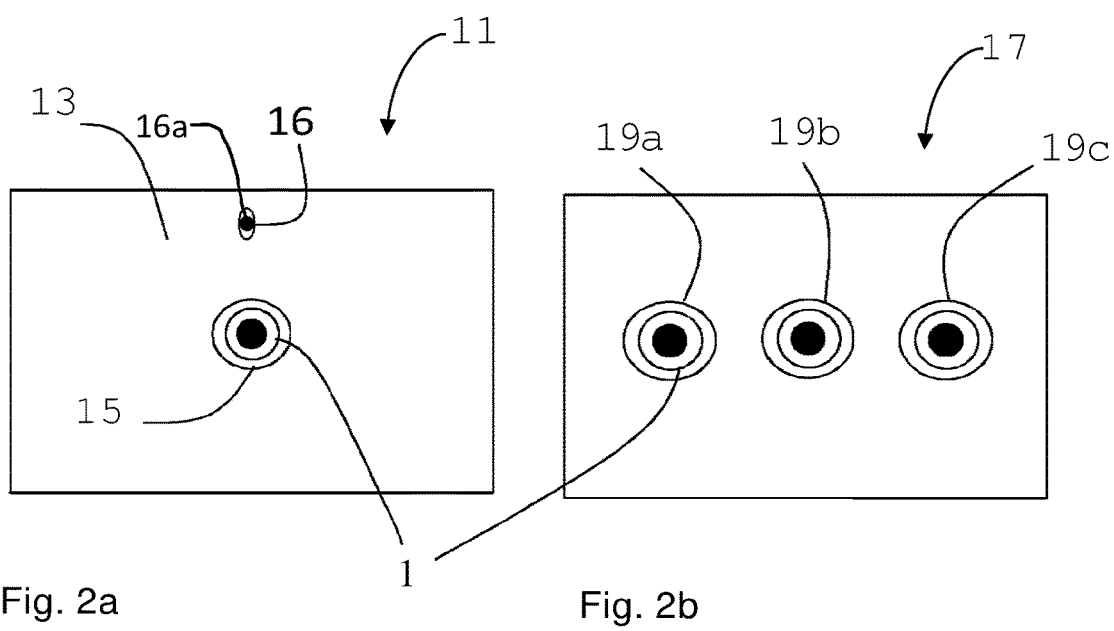
FIGS. 2A and 2B show schematically a base station of a bioreactor system according to two different embodiments of the invention comprising one or three temperature sensor means.
Figure 3:
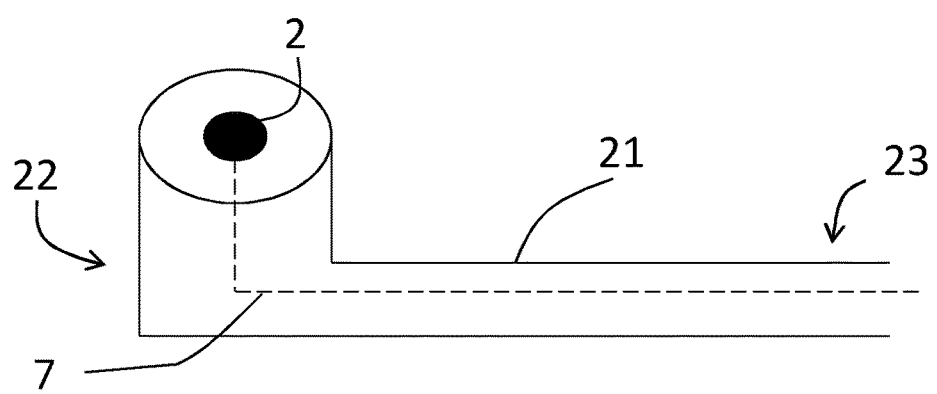
FIG. 3 shows schematically an arm comprising a temperature sensor means according to an embodiment of the invention, the arm being adapted to be used in a base station of a bioreactor system.

FIG. 1 shows schematically a temperature sensor means 1 according to one embodiment of the invention. The temperature sensor means comprises a thermally conducting layer 2 arranged to face the surface to be measured, a thermally insulating layer 3 attached to the thermally conducting layer 2 on the opposite side to the surface to be measured and a temperature sensor 5 provided between the thermally conducting layer 2 and the thermally insulating layer 3 and being completely surrounded on all its sides by either the thermally conducting or thermally insulating layers. The thermally conducting layer is a material with higher thermal conductivity than the thermally insulating layer. It could for example be a metal layer or a thermally conducting graphite or polymer layer. The temperature sensor 5 has a connection 7 through the thermally insulating layer to a control system. The thermally conducting layer 2 will improve the conductivity towards the surface to be measured and the thermally insulating layer 3 will decrease the influence from ambient temperature on the temperature sensor. In another embodiment of the invention the thermally conducting layer and/or the thermally insulating layer could be omitted FIGS. 2A and 2B shows schematically two examples of a base station of a bioreactor system according to the invention comprising one and three temperature sensor means as described in relation to FIG. 1 respectively. In FIG. 2A a base station 11 according to one embodiment of the invention is schematically shown. The base station to a bioreactor system comprises of course many more details but they are omitted in the description of embodiments of the present invention. In an embodiment the base station 11 comprises one temperature sensor means as described in relation to FIG. 1. Suitably the temperature sensor means 1 is provided on an arm 21 as shown in FIG. 3. The arm is provided inside the base station 11 under a base station upper surface 13. The arm 21 is provided such that the temperature sensor means can protrude up through an opening 15 in the base station upper surface 13. This can be achieved by providing the arm 21 as a lever. The temperature sensor means 1 is then provided onto one end 22 of the lever 21 and if something pushes down onto the other end 23 of the lever 21 the temperature sensor means 1 will move upwards and protrude through the opening 15 in the base station. Hereby the base station upper surface 13 also needs to be provided with another opening 16 for receiving a pushing means 16a that will push the end of the lever opposite the temperature sensor means downwards. A tray adapted to hold a bioreactor and to be positioned onto the base station may comprise this one or more pushing means. Another possible design would be to provide the temperature sensor means 1 on a resilient arm 21 which protrudes up through the opening 15 in the base station upper surface 13 but easily is pushed back if something presses on the temperature sensor means 1 from above. In FIG. 3 an arm 21 with a temperature sensor means 1 is shown. This arm could be provided in the base station as described above either as a lever or as a resilient arm. In FIG. 3 a communication connection 7 from the temperature sensor through the thermally insulating layer 3 is shown.

In FIG. 2B a base station 17 according to another embodiment of the invention is schematically shown. In this embodiment three arms 21 comprising temperature sensor means are provided. Hereby also three openings 19a, 19b, 19c are provided in the base station upper surface. If the arms are of the lever type three openings corresponding to the opening 16 of FIG. 2A should also be provided.

Figure 4A:
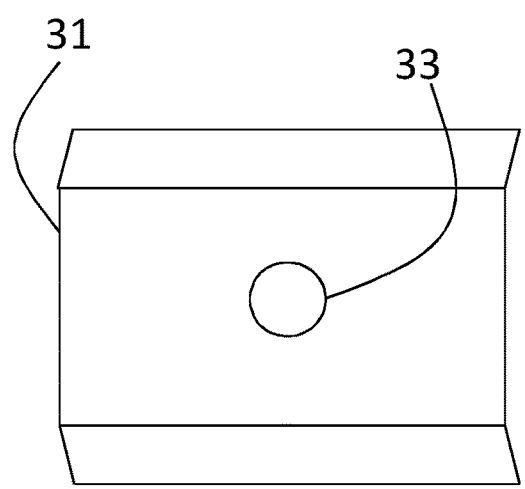
FIGS. 4A and 4B show schematically trays adapted to be provided on a base station according to an embodiment of the invention and the trays being adapted to hold bioreactor bags.
Figure 4B:
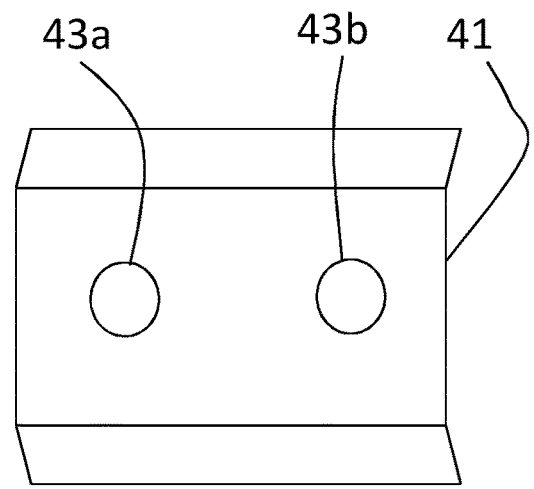

FIGS. 4A and 4B shows schematically trays adapted to be provided on a base station according to embodiments of the present invention and the trays being adapted to hold bioreactor bags. The tray 31 of FIG. 4A can be used in either the base station 11 shown in FIG. 2A or the base station 17 shown in FIG. 2B. The tray 31 is adapted to hold a bioreactor bag and the tray comprises an opening 33 positioned to align with the opening 15 of the base station 11 of FIG. 2A and the middle opening 19b of the base station 17 of FIG. 2B. Suitably the opening 33 in the tray is somewhat larger than the temperature sensor means. Hereby the temperature measurements will be less effected by the heaters that often are provided in the trays. When the tray 31 of FIG. 4a is used together with the base station 17 of FIG. 2B the two other temperature sensor means provided through openings 19a, 19c will not be protruding up through the openings because the tray 31 does not comprise corresponding pushing means for these temperature sensor means arms (if the lever variant is used). If resilient arms instead are used the temperature sensor means provided through the openings 19a and 19c will be pushed downwards by the tray 31 and not be used.

The tray 41 of FIG. 4B can be used in the base station 17 shown in FIG. 2B. The tray 41 comprises two openings 43a, 43b to receive one temperature sensor means 1 each. In this embodiment the temperature sensor means 1 provided through the middle opening 19b of the base station 17 will not be used and the temperature sensor means provided through the opening 19a will protrude up through the opening 43a of the tray 41 and the temperature sensor means provided through the opening 19c will protrude up through the opening 43b of the tray 41. In this embodiment two bioreactor bags could be provided in the tray 41. The openings in the trays 33, 43a, 43b can in one embodiment be covered by a suitable thin film, for example a plastic film. This could be beneficial in order to keep any spillage in the tray. However this is not necessary.

A control system of the bioreactor system comprises in one embodiment means for measuring the ambient temperature and means for compensating the bioreactor temperature measurement for different ambient temperatures.

In an embodiment, the temperature sensor or sensors are provided in the base station instead of in the different trays. Hereby the trays can be kept simple and without any need for calibration and electrical connections. It is beneficial to have all of these functions in the base station.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A bioreactor system comprising:
   a base station comprising a temperature sensor means positioned in an opening on the upper surface of the base station, a control system, and a communication connection between the temperature sensor means and the control system,
   wherein the temperature sensor means comprises a first side, a second side opposite the first side, a third side connecting the first and the second sides, and a temperature sensor,
   wherein the first side comprises a thermally conducting layer arranged to face a surface to be measured, the second side comprises a thermally insulating layer on an opposite side of the surface to be measured, and the third side comprises a thermally insulating layer,
   wherein the thermally conducting layer and the thermally insulating layer sandwich the temperature sensor therebetween, the temperature sensor being surrounded on all its other sides by the thermally insulating layer,
   a tray exchangeably attached to the base station to house a bioreactor bag,
   wherein the tray comprises a heater and at least one opening that substantially aligns with the opening on the upper surface of the base station for receiving the temperature sensor means such that the first side of the temperature sensor means will contact a surface of the bioreactor bag when the bioreactor bag is provided in the tray, and
   wherein the opening in the tray is larger than the temperature sensor means such that the temperature sensor is less affected by the heater provided in the tray.

2. The bioreactor system of claim 1, wherein the temperature sensor is mounted on one end of an arm being a lever with the other end of the arm connected to a pushing device provided on the tray such that when the pushing device is pushed down by a force independent of the bioreactor bag, the temperature sensor will move upwards through the opening in the tray such that the temperature sensor will contact the bioreactor bag surface but not disturb the bioreactor bag surface.

3. The bioreactor system of claim 1, wherein the base station comprises more than one temperature sensors each positioned in an opening on the upper surface of the base station and the opening(s) in the tray that align with the opening(s) in the base station allows the temperature sensor(s) positioned therein to contact the bioreactor bag surface, whereby the other temperature sensor(s) optionally will be blocked by the tray and not contact the bioreactor bag surface.

4. The bioreactor system of claim 3, wherein each temperature sensor is mounted on a separate arm.

5. The bioreactor system of claim 1, wherein the control system comprises a device for compensating the temperature measurement for the ambient temperature.

6. The bioreactor system of claim 1, wherein
   the bioreactor system is calibrated and only the base station and not the tray holding the bioreactor bag is considered for calibration.

7. The bioreactor system of claim 1, wherein the thermally conducting layer is a material having higher thermal conductivity than the thermally insulating layer.

8. The bioreactor system of claim 1, wherein the thermally conducting layer is a metal or a thermally conducting graphite or polymer.

9. The bioreactor system of claim 1, wherein the base station comprises three temperature sensors each positioned in an opening on the upper surface of the base station and the tray comprises two openings align with two of the three openings of the base station such that the two temperature sensors positioned therein can protrude and respectively contacting the surface of two bioreactor bags, whereby the third temperature sensor will be blocked by the tray and not contacting the surface of any bioreactor bags.

10. The bioreactor system of claim 1, wherein the tray comprises two openings to receive one temperature sensor each.

11. The bioreactor system of claim 1, wherein two bioreactor bags are provided that each in contact with one temperature sensor.

12. The bioreactor system of claim 1, wherein there are three temperature sensors and the tray comprises one opening to receive one of the three temperature sensors.

\* \* \* \* \*